United States Patent [19]

Lew et al.

[11] Patent Number: 4,785,245

[45] Date of Patent: Nov. 15, 1988

[54] RAPID PULSE NMR CUT METER

[75] Inventors: Hyok S. Lew, Arvada; Gerald L. Schlatter, Boulder, both of Colo.

[73] Assignee: Engineering Measurement Company, Longmont, Colo.

[21] Appl. No.: 906,749

[22] Filed: Sep. 12, 1986

[51] Int. Cl.$^4$ ............................................. G01R 33/20
[52] U.S. Cl. ..................................... 324/308; 324/307; 324/314; 324/319; 324/321; 436/173
[58] Field of Search ............... 324/307, 306, 308, 314, 324/319, 320, 321, 309; 436/173, 146

[56] References Cited

U.S. PATENT DOCUMENTS

| | | | |
|---|---|---|---|
| 2,999,976 | 9/1961 | Francis et al. | 324/307 |
| 3,525,030 | 8/1970 | Béné | 324/307 |
| 3,729,674 | 4/1973 | Lowderslager | 324/307 |
| 4,291,271 | 9/1981 | Lauffer | 324/307 |
| 4,532,217 | 7/1985 | Springer, Jr. et al. | 324/307 X |
| 4,551,679 | 11/1985 | Bossaert | 324/307 X |
| 4,618,827 | 10/1986 | Redington et al. | 324/309 |
| 4,644,279 | 2/1987 | Hoshino et al. | 324/307 X |
| 4,654,594 | 3/1987 | Sepponen | 324/307 X |
| 4,687,659 | 8/1987 | Quay | 436/173 X |
| 4,701,708 | 10/1987 | Hardy et al. | 324/308 X |
| 4,706,024 | 11/1987 | Dumoulin | 324/309 |

OTHER PUBLICATIONS

J. Trumbetas, J. A. Fioriti, and R. J. Sims, "Study of Lipid-Protein Interaction Using Pulsed NMR", Journal of the American Oil Chemists' Society, vol. 56, No. 10, pp. 890-893 (1979).

W. H. Vander Heyden and F. Toschik, "The Nuclear Magnetic Resonance Flowmeter, A Simplified Design", (date unknown), but by Jan. 1988, pp. 857-864.

W. K. Genthe, W. R. Vander Heyden, J. H. Battocletti, W. S. McCormick, and H. M. Snowball, "NMR Applied to Flow Measurement", R-114 from Instrumentation Technology (date unknown), but by Jan. 1988; 6 pages.

Badger Meter, Inc., Precision Products Division Circular, undated, "Badger Model MRF II Magnetic Resonance Flowmeter", (date unknown), but by Jan. 1988.

Badger Meter, Inc., Equipment Manual MRF II, 1973; Ref. AR, 4 total pages.

R. J. S. Brown and B. W. Gamson, "Nuclear Magnetism Logging", Petroleum Transactions, AIME, vol. 219, pp. 199-207 (1960).

A. Timur, W. B. Hempkins, and G. R. Massey, "Analysis of Sidewall Samples by Nuclear Magnetic Resonance Methods," paper presented at SPWLA Twelfth Annual Logging Symposium, May 2-5, 1971, pp. 1-21.

(List continued on next page.)

[57] ABSTRACT

The invention relates to a method and an apparatus for determining the cut (percentage) of one component of a multiphase fluid flowing in a pipeline, for example, oil or other hydrocarbon in a fluid flow that comprises oil, water, gas, and soil components, by use of NMR analysis. The fluid is flowed through an apparatus specifically designed to perform the analysis on the flowing fluid. Carefully sequenced 90° pulse series are used to take advantage of the different spin relaxation times of the selected atomic species when they are constituent parts of molecules having inherently different levels of random molecular motion. The timing between pulses in a series and between series of pulses is chosen so that NMR emissions from unwanted matter do not occur, and FID peaks from the desired matter are registered. The FID peak amplitude of the measured component of the flowing fluid is then compared to the FID peak amplitude of a 100% sample of the component, with the resulting ratio being directly related to the percentage of the component in the flowing fluid. In this way, a direct and highly accurate measure of the desired component, oil for example, is achieved on a real-time basis in the field, without the need to interrupt operations. Results of these measurements can be used with total flow meters to derive an accurate measure of flow rates of the desired component.

OTHER PUBLICATIONS

B. L. Madison & R. C. Hill, "Determination of the Solid Fat Content of Commercial Fats by Pulsed Nuclear Resonance," reprinted from Journal of the American Oil Chemists' Society, vol. 55, No. 3, pp. 328-331 (1978).

"Total Computer Capability in Solid Fat Determinations", undated advertising brochure, Praxis Corp., San Antonio, TX (date unknown), but by Jan. 1988; 2 pages.

"Determine Oil, Fat or Moisture Content in Seconds," undated advertising brochure from IBM Instruments, Inc., Danbury, Conn.

"Determination of the Oil and Water Content of Rice by Pulsed NMR", advertising brochure from IBM Instruments, Inc., Danbury, CT (1983), 1st brochure, 1 page, published by Jan. 1988; 2nd brochure with Julie M. Shih, 2 pages.

"Successive Oil, Water Determinations," EDM Descriptions J-73, IBM Instruments Lab, Danbury, CT (date unknown), but by Jan. 1988; 1 page.

*Primary Examiner*—Tom Noland
*Attorney, Agent, or Firm*—James R. Young

17 Claims, 12 Drawing Sheets

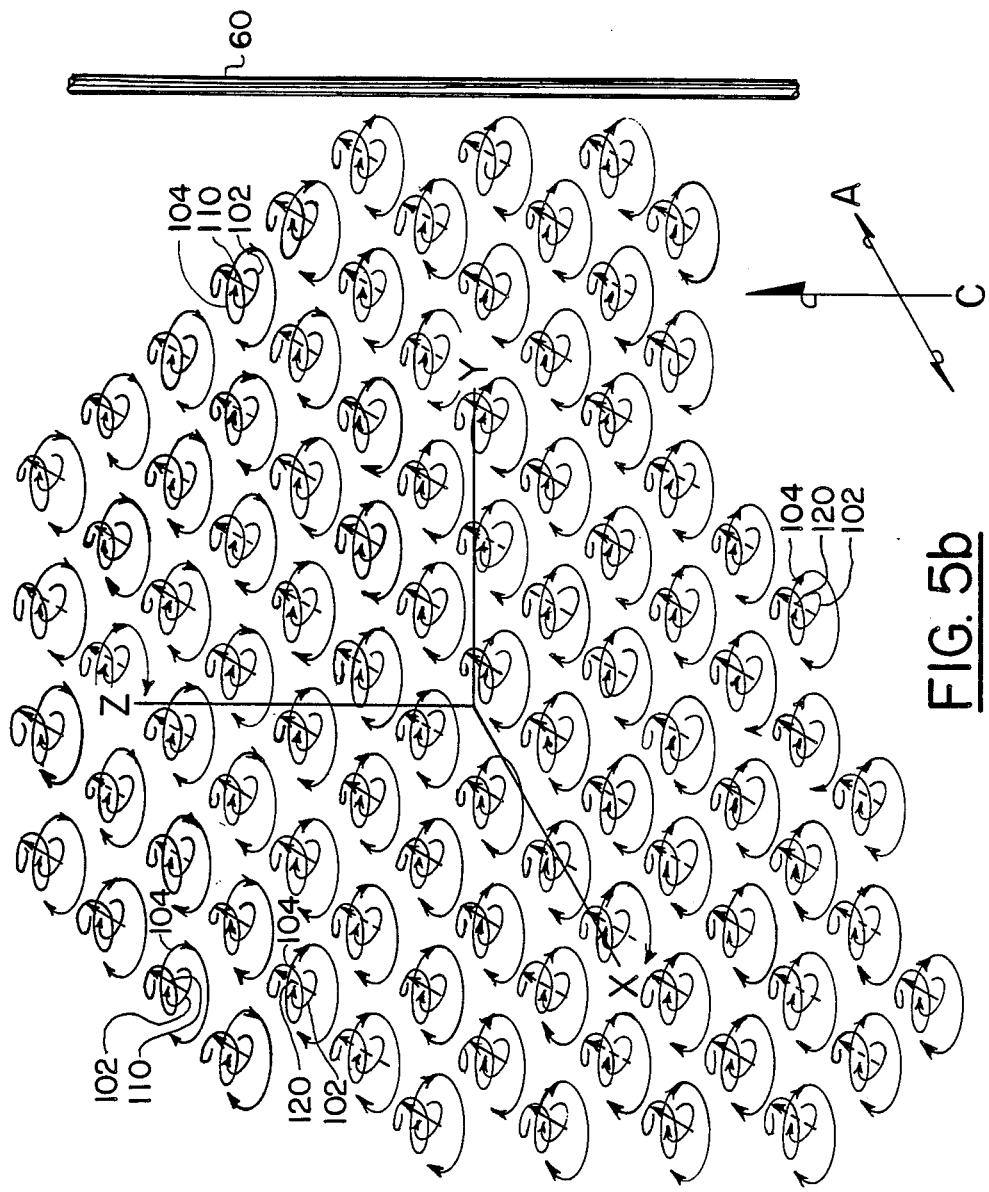

RAPID PULSE NMR CUT METER

BACKGROUND OF THE INVENTION

1. Field of the Invention

The present invention relates to nuclear magnetic resonance (NMR) material analysis, and more specifically to a method and apparatus for determining the amount of a material having a first molecular species, such as an organic material, in a mixture containing another molecular species, such as an aqueous material, wherein both molecular species have a common atomic species, such as hydrogen.

2. Description of the Prior Art

There are many situations in a variety of industries, ranging from research activities to production material measurements, and the like, wherein it is necessary, or at least very desirable, to be able to determine the amounts of various materials or molecular species in a mixture. For example, it is often desirable to be able to determine and measure quickly the relative amounts of organic and nonorganic materials in a mixture such as for quality control or for recording the amounts of such materials present in the mixture as a basis for production records, sales of materials, production performance and cost/benefit analyses, as a basis for royalty payments, and the like.

One such industry in which there has been a need for decades for a practical, reliable, yet high quality and accurate method and apparatus for distinguishing and measuring the amount of organic material in a mixture is the oil industry. Crude oil is typically produced from wells drilled into geological formations that also contain various amounts of salt water and other impurities. In practice, it is difficult, and in most situations impossible, to produce crude oil from the wells without also producing substantial quantities of salt water along with the oil. Typically, such production includes a mixture of crude oil, gas, and salt water, along with varying smaller amounts of other impurities, such as sand, clay, sulfur, salt, minerals, and other materials, depending to some extent on the character and content of the formation. Such mixtures flow typically in a two-phase, or sometimes even three-phase, flow that is seldom uniform or homogeneous and can vary in proportions over time, sometimes in an erratic manner. Yet, there has been for many years a great deal of need to be able to determine and measure the exact amount of crude oil being produced by a well, both on a continuous basis and on a spot or instantaneous basis.

The simplest method of determining amounts of oil in a mixture of materials produced by a well is to separate the oil from the gas, water, sand, mud, and other materials in the mixture and then measure it. The fraction of the oil in the total mixture, i.e., the oil cut of the mixture, can be determined by comparing the volume of oil to the volume of the total mixture. However, conventional processes for separating oil from the other constituents of the well production mixture require substantial time, equipment, and effort and does not provide a measurement of oil cut on a real time continuum basis.

There are several types of oil-cut meters available, the better known of which measure oil-cut of the well production by determining the reflection or transmission of radio frequency (rf) electromagnetic waves. However, such meters are really water-cut meters, instead of oil-cut meters. Water is electrically conductive, while oil is a dielectric medium. Such meters determine water-cut as a function of varying conductivity and dielectric constant of the mixture, then subtract the water cut from the total to determine oil cut. One of the basic fallacies or margins of error for this approach is that it assumes that whatever is not water in the mixture is oil. That assumption classifies as oil all other impurities, such as sand, mud, and the like, in the mixture that is not water. Obviously it is not an assumption on which accurate data can be based.

Another basis for inaccuracy in such prior art meters is that the degree of reflection or transmission of the radio frequency waves varies as a function of the sizes and shapes of the water drops suspended in the mixture. Also, the conductivity of water varies sensitively as a function of dissolved ions, which can fluctuate significantly. Therefore, there is no direct one-to-one relationship between the actual wave reflection or conductivity measurement and the actual water-cut. Consequently, there is a substantial margin of error in the water-cut measurement itself even before it is subtracted from the total where the other potential for significant error is introduced by assuming incorrectly that all that is not water is oil, as described above. As a result, such prior art water-cut meters disguised as oil-cut meters are not very accurate or reliable and have only limited utility in the industry.

There is another meter available that also measures water-cut and gas in the well production mixture, wherein the cut ratio is obtained from the bulk density of the total mixture and the bulk density of a degassed sample. In this kind of so-called "three-phase flowmetering", a large error can be introduced either by the degassed sample not representing accurately the bulk flow, by the heavy impurities, such as mud and sand, or by fluctuations in the density of the oil produced in some oil wells. A small change in oil density can result in a large error because the density of oil is close to that of water.

Nuclear magnetic resonance (NMR) analysis can be a powerful tool in detecting and determining the amounts of aqueous materials (water or water based materials) in a mixture. It is known that hydrogen atoms in both the aqueous material and the organic material emit rf waves of the same Larmor frequency intrinsic to the hydrogen atom. However, the rf emission from the hydrogen atoms in the organic material decays much faster than the rf emission from the hydrogen atoms in the aqueous material.

For example, the spin-spin relaxation time of typical organic liquid, such as oil, is about 50 milliseconds while the spin-spin relaxation time of water is about three (3) seconds. Therefore, the initial maximum amplitude of the rf emission from an aqueous-organic mixture is the sum of the rf emissions from both the aqueous and the organic components. However, after about one-half ($\frac{1}{2}$) minute, the rf emission from the organic component has decayed or attenuated by about 99.9% and effectively disappeared so that a measurement of total rf emission at that time comprises essentially rf emission from the aqueous component only.

Then, the initial amplitude of the rf emission from the aqueous component only can be determined mathematically by utilizing the curve of decaying or attenuating rf emissions measured by a method called "spin echo" and extrapolating that aqueous component curve backwards in time to the initial rf emission start point. Once the initial amplitude of the rf emission of the aqueous component is obtained in this spin echo measurement-/reverse time mathematical extrapolation manner, it can be subtracted mathematically from the actual initial measurement of the total rf emission of the mixture to determine the initial amplitude of the rf emission from the organic component. Finally, the amount of each component can be determined by comparing the initial maximum amplitude of the rf emission from each component with a measured standard rf emission of that component of known quantity.

While such conventional NMR analysis technique, as described above, can be used in the analysis of aqueous-organic mixtures, it suffers from several shortcomings. Specifically, this conventional NMR technique is based on the large difference between the respective spin-spin relaxation times of the aqueous and the organic components in the mixture, which phenomenon is very sensitive to temperature. Therefore, if the temperature of the mixture is not closely and accurately monitored and controlled, a large error can result in the process of extrapolating the initial maximum amplitude of the rf emission from the aqueous component. Also, the amount of aqueous component, i.e. water-cut, is determined first by the extrapolation from the rf emission, while the amount of organic component is computed by subtracting the extrapolated initial aqueous rf emission from the total initial rf emission. Therefore, like the water-cut meters disguised as oil-cut meters described above, this conventional NMR analysis method is really a watercut meter as far as the analysis of the aqueous-organic mixture is concerned. It does not detect and analyze the rf emission from the organic component in a direct method.

Therefore, there is still a substantial need in the industry, which has persisted for decades but never been met, for an oil-cut meter that can measure oil volume fraction directly from the oil in the mixture without relying on a water-cut valve. That need includes the requirement for an oil-cut meter that can operate and provide measurements on a continuous real-time continuum as well as on an instantaneous basis.

SUMMARY OF THE INVENTION

Accordingly, it is a general object of the present invention to provide a method and apparatus for detecting and measuring the fraction of a first material, such as oil, in a mixture having another material, such as water, by detecting the first material directly.

A more specific object of the present invention is to provide a method and apparatus for detecting and measuring accurately and reliably the fraction of oil in a two-phase medium, such as in oil-water, oil-sand, or oil-gas mixtures or in other multi-phase mediums, such as oil-water-gas, oil-sand-gas, or oil-water-sand-gas mixtures.

Another specific object of the present invention is to provide a method and apparatus for detecting the fraction and net amount of oil in a flowing mixture on a continuous real-time continuum basis, as well as on an instantaneous basis.

Still another specific object of this invention is to provide an accurate and reliable oil-cut meter that can be installed in an oil well flow line, gathering network line, or other flow pipe for continuously or instantaneously detecting and measuring on a real-time basis the oil-cut and net amount of oil in a mixture of materials, including water, gas, sand, and mud produced from an oil well.

A further object of the present invention is to provide a method and apparatus for determining the fraction and net amount of a first material in a mixture that includes the first material and a second material, wherein the first and second materials have different molecular species with a common atomic species and the NMR spin-lattice relaxation times for the molecular species are different from each other.

Additional objects, advantages, and novel features of the present invention will be set forth in part in the description that follows, and in part will become apparent to persons skilled in the art upon examination of the following or may be learned by the practice of the invention. The objects and advantages of the invention may be realized and attained by means of the instrumentalities and in combinations particularly pointed out in the appended claims.

To achieve the foregoing and other objects and in accordance with the purpose of the present invention as embodied and broadly described herein, the method of this invention may comprise the steps of continuously exposing a mixture that includes a first material and a second material to a strong constant magnetic field in one direction, simultaneously exposing the mixture to a weak alternating magnetic field in a different direction, for a short period, wherein the oscillating frequency of the weak alternating magnetic field is substantially equal to the Larmor frequency of an atomic species that is common to the different molecular species of the first and second materials. In a mixture of organic and aqueous materials, the Larmor frequency can be that of hydrogen. The method also includes the steps of applying the alternating magnetic field in rapid intermittent pulses, wherein the duration of each pulse is long enough to reorient the magnetic moments of the common atomic species in the different molecular species of the mixture away from the positions parallel to the constant magnetic field, and the time interval or pause between each pulse is long enough to allow substantial relaxation of the nuclei magnetic moments of the common atomic species of one of the molecular species, but too short to allow any significant relaxation of the nuclei magnetic moments of the common atomic species in the other molecular species. The method also includes the steps of detecting and measuring the rf emissions from the mixture between pulses, which are emitted almost entirely by the material component that experiences substantial relaxation to the virtual exclusion of the material component that experiences no significant relaxation between pulses. In an organic-aqueous mixture, the rf emission is almost entirely from the organic component and almost none from the aqueous component. Then, by comparing the amplitude of the rf emission, preferably the initial maximum amplitude, i.e., FID peak, to corresponding amplitude or FID peak of an rf emission derived from a sample of 100% of the material component being measured, e.g., oil, under the same analysis conditions, the actual fraction or cut of that material in the mixture can be determined.

The method can also include flowing the mixture on a continuous real-time basis through the analysis conditions of this invention to obtain a real-time fraction or cut continuum of the material component being detected and measured. This real-time cut continuum can be used with a corresponding real-time continuum of total volumetric flow of the mixture to determine actual volume of the measured component, such as oil, that flow through the analyzer system in any desired period of time or the flow rate of the component material at any desired instant in time.

The apparatus of this invention may comprise a container, preferably in the form of a flow-through conduit, a strong magnet positioned adjacent the container and having a strong constant magnetic field oriented in one direction through the container, an electromagnet or transmission coil also positioned adjacent the container in the vicinity of the constant magnetic field for providing a weak alternating magnetic field oriented in a second direction through the container, and an antenna or a receiver coil for detecting rf emissions from a mixture in the container exposed to the magnetic fields. A frequency controller or rf generator energizing the transmission coil sets the frequency of the alternating magnetic field to about the Larmor frequency of a common atomic species in the two different molecular species of the material components in the mixture being analyzed in the container. For example, for an organic-aqueous mixture, the frequency can be set at the Larmor frequency of hydrogen. A pulse controller or generator connected to a switch between the rf generator and the rf transmission coil causes the alternating magnetic field to be applied in intermittent pulses of predetermined duration with predetermined pauses or time intervals between the pulses. The pulse durations are set to be long enough to tilt the nuclei magnetic moments of the common atomic species from the direction of the constant magnetic field to a plane including the direction of the alternating magnetic field. The pauses time intervals between pulses is long enough to allow the nuclei magnetic moments to recover back to the direction of the constant magnetic field in one of the material components of the mixture, such as the organic material, but too short to allow any significant recovery of the nuclei magnetic moments in the other material component, such as the aqueous material.

BRIEF DESCRIPTION OF THE DRAWINGS

The accompanying drawings, which are incorporated in, and form a part of, the specifications illustrate the preferred embodiments of the present invention, and together with the description serve to explain the principles of the invention.

In the drawings:

FIGS. 5a-5g are progressional diagrammatic representations of the series of phases of the motion of nuclear magnetic moments in two different materials to produce NMR emission from one of the materials according to the invention.

DETAILED DESCRIPTION OF THE PREFERRED EMBODIMENT

Figure 1:
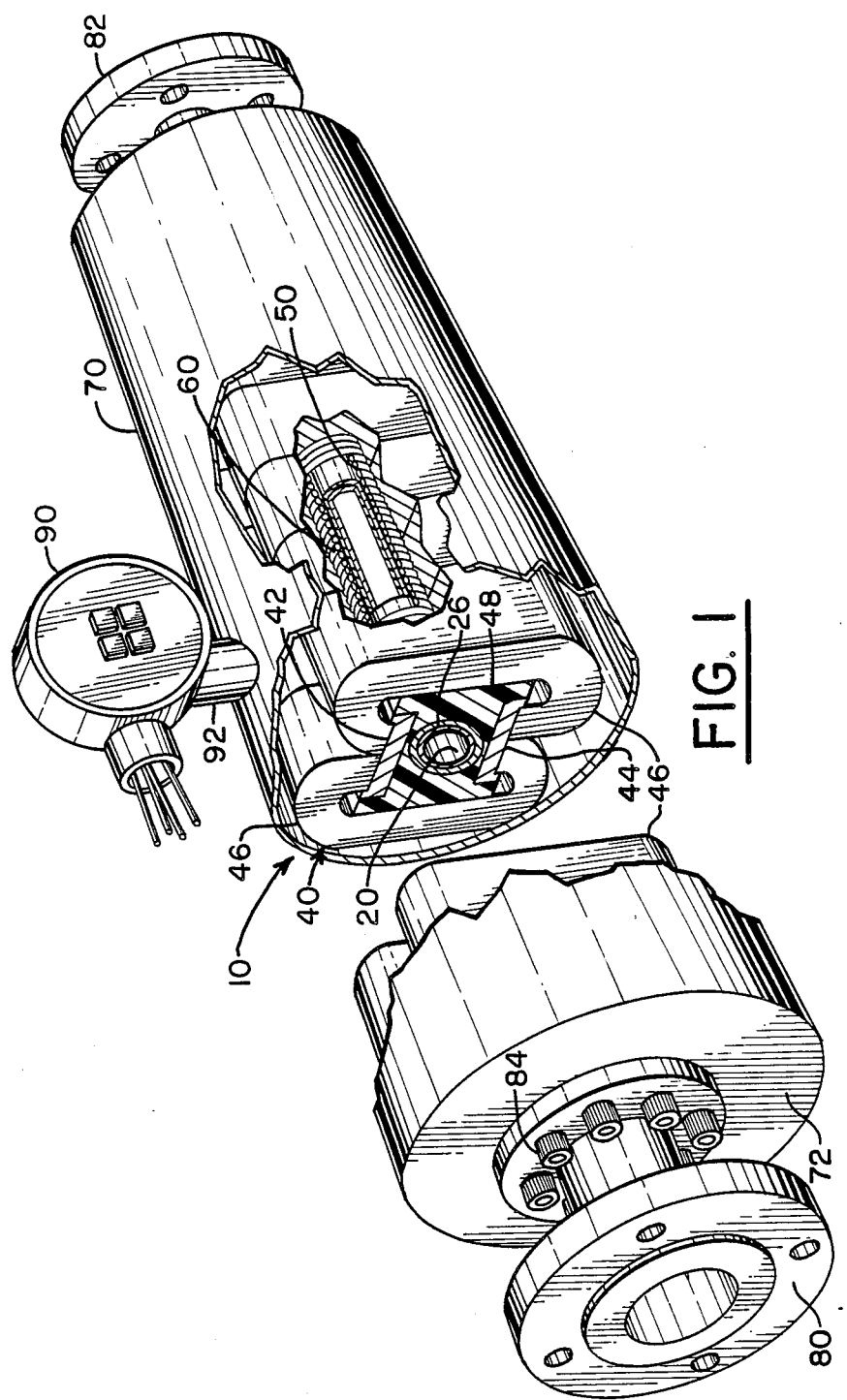
FIG. 1 is an isometric view of the rapid pulse cut meter probe according to the present invention with portions of the external shell and other components cut away to reveal the structures of internal components.
Figure 2:
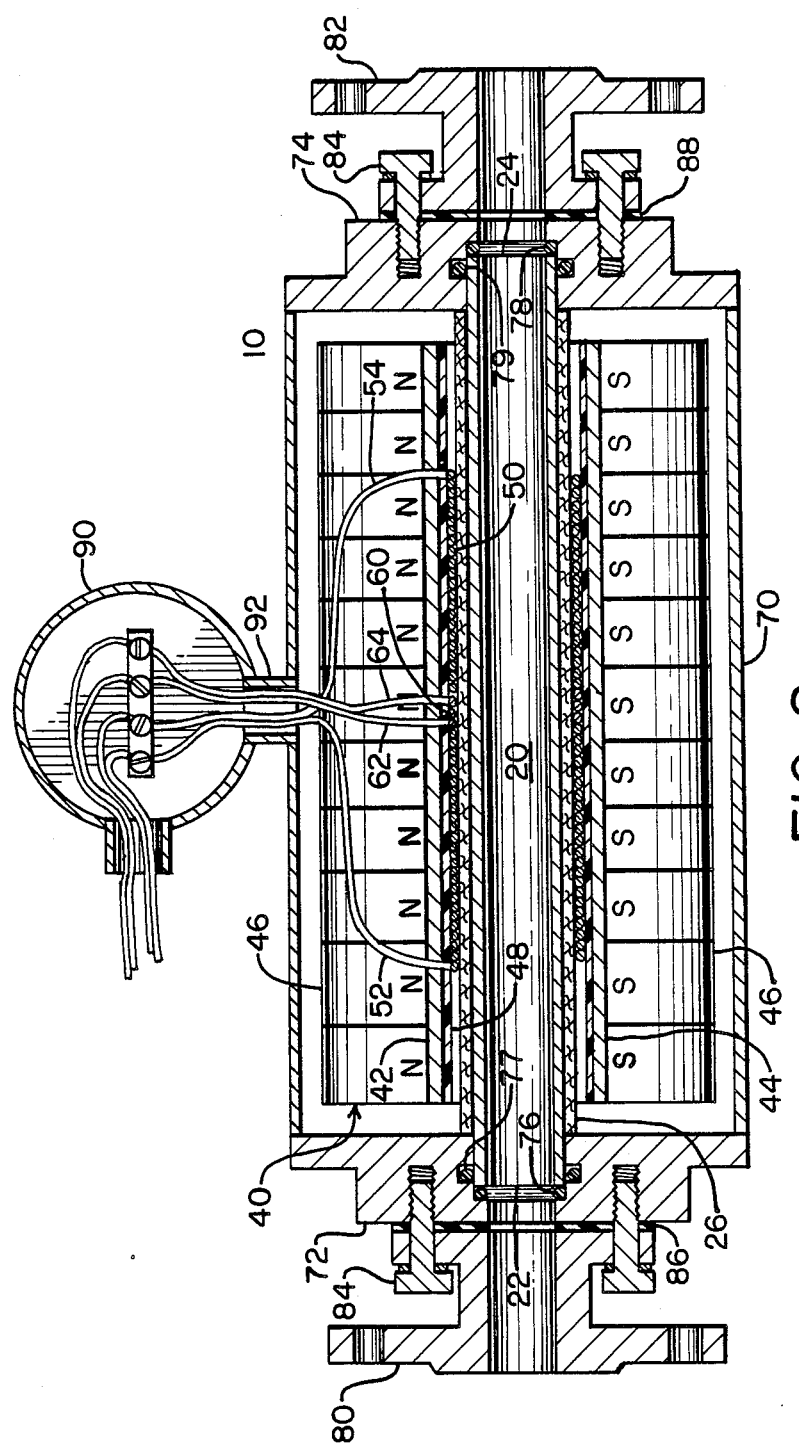
FIG. 2 is a cross sectional view of the rapid pulse cut meter probe of the present invention.

A rapid pulse cut meter probe 10 according to the principles and to facilitate the practice of the present invention is shown in FIGS. 1 and 2. The principles of the operation of the rapid pulse cut meter probe 10 will be described in more detail below. However, for purposes of a general description of the major components, the probe 10 is comprised of container, preferably in the form of an elongated hollow tube 20, that extends from one end of the probe 10 to the other. A permanent magnet bank 40 is positioned around the tube 20 in a position to create a strong, constant magnetic field in a first direction, preferably transversely, through the tube 20. The magnet bank 40 can be comprised of two permanent bar magnets 42, 44 positioned diametrically opposite each other along the length of the tube 20, as shown in FIGS. 1 and 2, with a plurality of C-shaped carbon steel flux paths 46 connecting one bar magnet 42 to the other bar magnet 44. Of course, other suitable magnetic field producing means, such as horseshoe or C-magnets, electromagnets, flexible magnet impregnated rubber-like material, and the like, can be used for this purpose.

Figure 3:
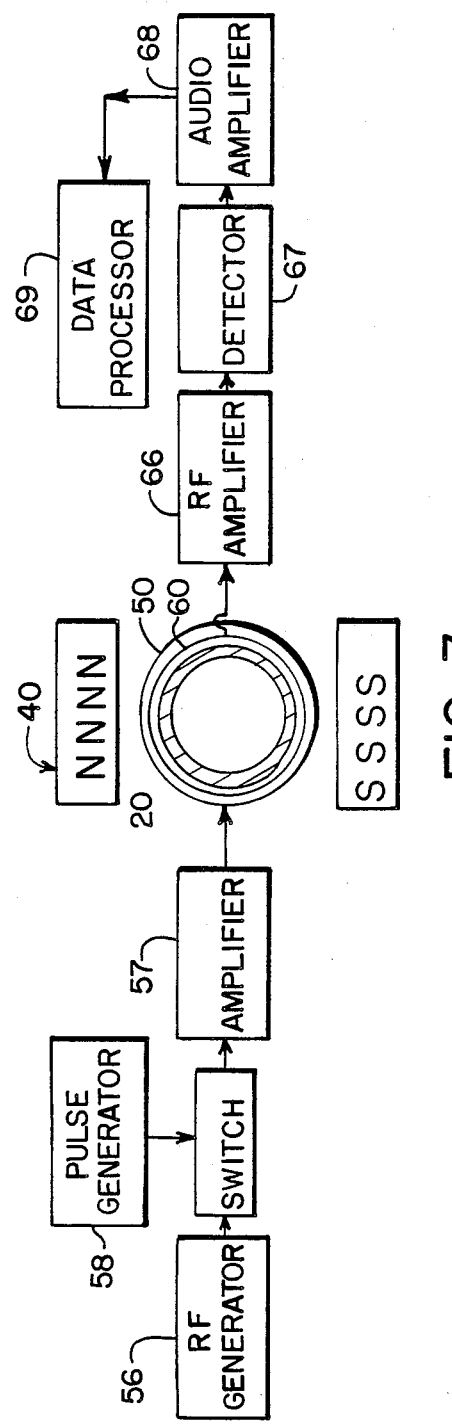
FIG. 3 is a block flow diagram of the principal control components of the present invention.

A transmission coil 50 is comprised of insulated electric conductor wires wound around the periphery of the tube 20 for producing an alternating magnetic field in a different direction than the constant magnetic field produced by the magnet banks 40, 42. The transmission coil 50 extends along a substantial length of the tube 20, but preferably not as long as the constant magnet bank 40. In this preferred configuration, the transmission coil 50 creates an alternating magnetic field through the tube 20 in the direction of the longitudinal axis of the tube 20, which is perpendicular to the constant magnetic field. The transmission coil 50 is connected via wires 52, 54 to an external frequency controller or rf generator, generally indicated as 56 in FIG. 3. A pulse controller or generator 58 is also required, for setting and controlling durations and periods of intermittent pulses of alternating current to the transmission coil 50. As shown in FIG. 3, the pulse generator 58 can be connected to a switch 59 that is located between the rf generator and the transmission coil 50 for interrupting the rf current to the coil 50. An amplifier 57 can be used to boost the rf transmission to the coil for a stronger alternating magnetic field. All of these components 56, 57, 58, 59 can be state-of-the art devices, so further description of them is unnecessary.

A receiver coil or antenna 60 comprised of a much shorter coil wound around the peripheral surface of the tube 20 and is positioned at about midlength of the tube 20. This receiver coil 60 is for receiving nuclear magnetic resonance (NMR) emissions from a material in the tube 20. It is connected via wire leads 62, 64 to appropriate external amplifier 66, and processing components 67, 68, and 69 for purposes that will be described more fully below.

The major components described above can be enclosed in an elongated housing 70 that is attached at its opposite ends to respective end caps 72, 74. The opposite ends 22, 24 of tube 20 are also mounted for support in respective end caps 72, 74. The tube 20 is preferably fabricated with a non-magnetic and non-electrically conducting material, such as a ceramic or other suitable material that does not itself produce NMR emissions and does not inhibit or interfere with alternating field transmissions or distort NMR emissions to and from a material in the tube 20. Since this rapid pulse meter probe 10 is intended for use in high pressure conditions, it may be desirable to provide a reinforcing layer, such as cord wrapped jacket 26, around the periphery of the tube 20, particularly since many nonmagnetic materials, such as ceramics, do not have great tensile strength for resistance to pressure inside tube 20. O-ring seals 76, 77 in end cap 72 and O-ring seals 78, 79 in end cap 74 seal the ends of tube 20 from internal leaks.

Mounting flanges 80, 82 attached respectively to opposite end caps 72, 74 facilitate connecting the probe 10 into a fluid flow line (not shown), such as a production pipe from an oil well, or a branch or trunk gathering line (not shown) in an oil field gathering system, product line (not shown) in a factory, sample tube (not shown) in a laboratory, or the like. The flanges 80, 82 are fastened to the end cpas 72, 74 by bolts 84 and sealed by gaskets 86, 88, respectively.

The constant magnet bank 40 is mounted on a nonmagnetic seat 48 surrounding the tube 20. An enclosure 90 connected by conduit 92 to the interior of housing 70 provides a protected chamber for connecting lead wires from the probe components to external components of the system.

For purposes of describing the theory and operating principles of this invention, the classical electrodynamic theory of NMR will be used, although it is recognized that other theories of NMR, such as the quantum mechanical theory, may also be applicable. It is known, of course, that the nuclei of certain atoms exhibit phenomena similar to a spinning top made of a magnet. In other words, the nuclei of atoms with nonzero spin or parity possess an angular momentum and a magnetic moment. When a material comprised of these atoms is exposed to a strong constant external magnetic field, the nuclei magnetic moments experience magnetic torque that forces the nuclei magnetic moments to line up parallel to the external magnetic field. This alignment is often called the intermediate energy or equilibrium state. Also, such a nuclei magnetic moment precesses at an angular velocity equal to 2 times the Larmor frequency about an axis parallel to the external magnetic field.

Then, if the material is exposed to an alternating magnetic field perpendicular to the constant magnetic field, which alternating magnetic field oscillates at the same frequency as the rate of precession of the nuclei magnetic moment about the constant magnetic field known as the Larmor frequency, the nuclei magnetic moments tilt away from the direction parallel to the permanent magnetic field. Consequently, the nuclei magnetic moments precess following conical surfaces of increasing cone angle. The combined effect of the strong constant magnetic field and the weak alternating magnetic field oriented perpendicular to the constant magnetic field and oscillating at the Larmor frequency on the material comprising atoms of nonzero spin or parity is called "Nuclear Magnetic Resonance" or "NMR".

At atomic and molecular levels, physical attributes are understood and described more accurately in terms of statistical distributions or probabilities of certain physical phenomena occurring at any particular time or over certain intervals of time. However, statistical distributions or probabilities are difficult to illustrate. Therefore, while recognizing the limitations and inaccuracies inherent in illustrations of phenomena occurring at the atomic level, such illustrations are still helpful in describing such occurrences and in describing this invention.

Figure 4A:
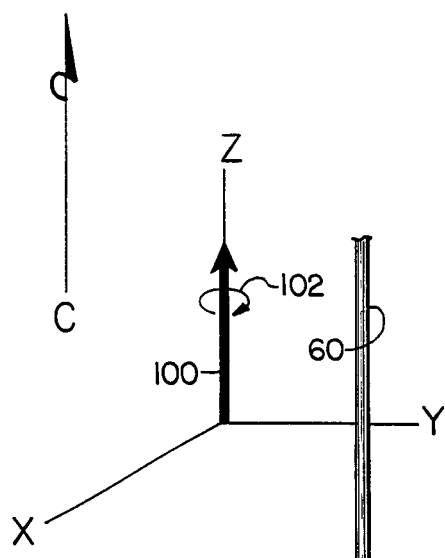
FIGS. 4a-4c are progressional diagrammatic representations of the motion of a nuclear magnetic moment producing an NMR emission.

Therefore, referring to FIG. 4a, in a material exposed to a strong constant magnetic field C, an appropriate explanatory concept is that a statistical probability of many nuclei magnetic moments 100 with an angular momentum associated with spin as indicated by rotation 102 will become oriented at an equilibrium orientation parallel to the Z-axis, which is parallel to the constant magnetic field C. There are a significant statistical number of such nuclei magnetic moments 100 maintained in the equilibrium position shown in FIG. 4a under the influence of the strong constant magnetic field C. This equilibrium position is also known as the intermediate energy state imposed by the constant magnetic field C.

Then, as a weak alternating magnetic field A is applied to the material in a direction perpendicular to the constant magnetic field A, the equilibrium is interrupted. Such an interruption by a comparatively weak magnetic field A would normally not have significant consequences. However, when the weak magnetic field oscillates at the same rate as the rate of the precessing motion of a nuclei magnetic moment 100, about the constant field C i.e., the Larmor frequency, the nuclei magnetic moments 100 tilt away from the Z-axis. Such alternating magnetic field at Larmor frequency can be described as having a similar effect on the nuclei magnetic moment 100 as tapping a spinning toy top from a direction lateral to the spin axis and precisely timed with the angular velocity of the precessing motion of the toy top. The tap induces the top to begin to wobble with its bottom point staying essentially stationary, but its top portion wobbling around the vertical axis as the top continues to precess about the vertical axis. If the top is tapped again and again at each wobble about the vertical axis, the wobble or tilt of the spin axis becomes more and more pronounced.

Figure 4B:
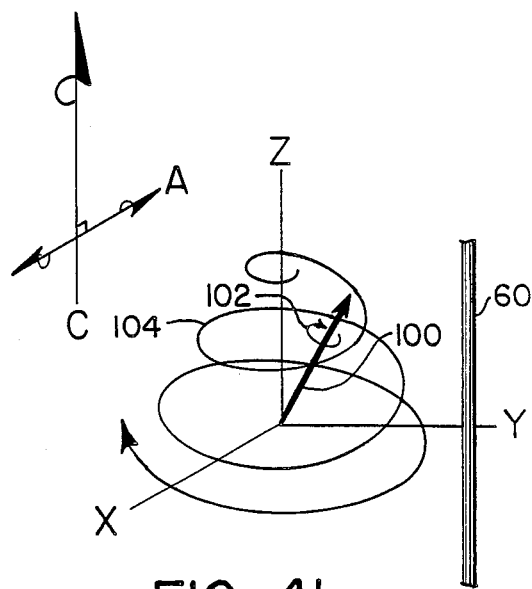

This effect on the spinning nuclei magnetic moment 100 is illustrated in FIG. 4b. As the alternating magnetic field A oscillating at Larmor frequency acts on the spinning nuclei magnetic moment 100, the nuclei magnetic moment 100 begins to tilt away from the Z-axis, while it maintains its axial spin 102. With continuing application of the alternating magnetic field A, the distal end of the nuclei magnetic moment 100 is driven further away from the Z-axis as it precesses around its proximal end where it intersects the Z-axis. The effect, as illustrated in FIG. 4b, is that the distal end of the precessing nuclei magnetic moment 100 is driven downwardly in a spiral pattern 104 toward the X-Y plane.

Figure 4C:
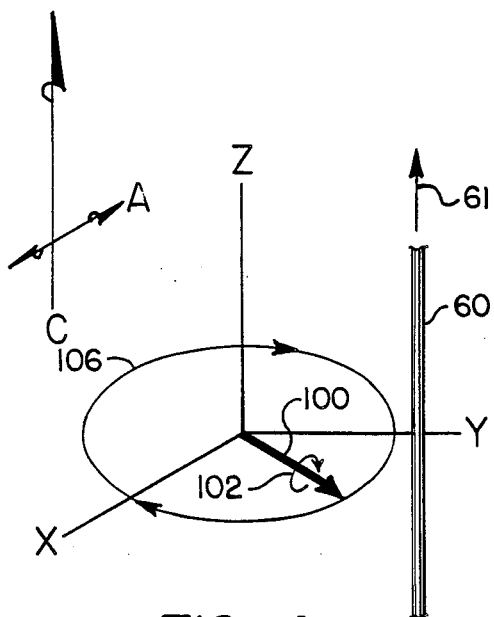
Figure 4D:
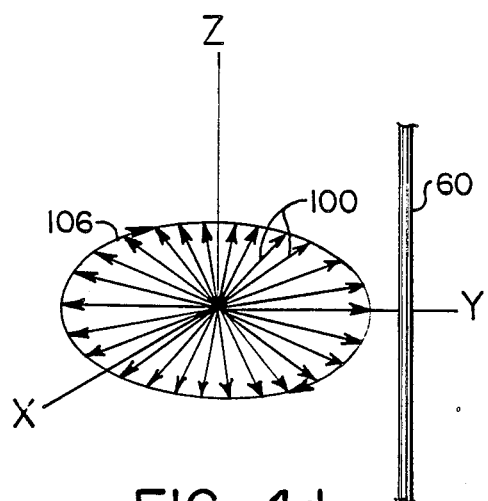

A pulse of alternating magnetic field A at Larmor frequency of sufficient duration to drive the nuclei magnetic moment 100 away from the Z axis to a precessing motion in an X-Y plane that is perpendicular to the Z axis, as illustrated in FIG. 4c, is called a 90 degree pulse. In this position, the distal end of the precessing nuclei magnetic moment 100 rotates in a circular path 106 like a radial spoke about its proximal end at the Z axis or hub. In such rotating position, the nuclei magnetic moment 100 has a sweeping magnetic field that can cut across an electrical conductor 60 positioned nearby, thereby inducing an electromagnetic potential or current 61 to flow in the conductor 60. Such a current 61 can, of course, be amplified, detected, and measured as an indication of the NMR emission.

A pulse of alternating magnetic field A oscillating at Larmor frequency tilts away the nuclei magnetic moments from the Z-axis towards the X-Y plane. In general, the vector representing the nuclei magnetic moments can be decomposed into the parallel component in the direction of the Z-axis and the normal component parallel to the X-Y plane. In equilibrium state under the constant magnetic field, the parallel component is equal to the maximum value, while the normal component is equal to zero. Immediately after a 90 degree pulse, the parallel component is equal to zero, while the normal component is equal to the maximum value. When the alternating magnetic field of 90 degree pulse is terminated, the parallel component starts to grow while the normal component starts to decay. Only the normal component produces NMR emission, since the parallel component with a constant orientation does not generate any alternating magnetic field. The decaying phenomenon of the normal component is called spin-spin relaxation. The growth of the parallel component is called spin-lattice relaxation (spin-lattice recovery may be more appropriate or descriptive terminology).

The measurements also show that within a very short time, the electromotive force induced in the receiver antenna or a conductor 60 decays to zero well before the normal component of the nuclei magnetic moments decay to zero. This phenomenon called free induction decay or FID is the result of randomizing directions of a large number of the precessing nuclei magnetic moments 100 in a material as the individual nuclear magnetic moment precesses at a precession velocity that is not uniform for all of the nuclei magnetic moments due to less than perfectly uniform constant magnetic field and other reasons.

The present invention takes advantage of both spin-spin relaxation rates and spin-lattice relaxation rates in a unique manner to discriminate between materials in a mixture that have different molecular compositions with a common atomic element. This basis of this invention is illustrated in FIGS. 5a–5g, again with the precaution that these illustrations are limited to imperfect, simplified representations of statistical probabilities of phenomena occurring on an atomic level.

In FIGS. 5a–5g, nuclei magnetic moments of two materials having different molecular compositions with a common atomic element are illustrated. The nuclei magnetic moments of the common atomic element in the first material are illustrated as a plurality of solid arrows 110. The nuclei magnetic moments of the common atomic element in the second material are illustrated as a plurality of broken arrows 120. The common atomic elements have the same angular momentum spin, as illustrated again by arrow 102, and they have the same magnetic moment; thus, they have the same Larmor frequency. However, the nuclear magnetic moments 110, 120 of the first and second materials, respectively, have different spin-spin relaxation rates and different spin-lattice relaxation rates. For example, a first material could be an organic material, such as oil, and the second material could be an aqueous material, such as water. Both the oil and the water have hydrogen atoms, but they have different molecular compositions. The nuclear magnetic moments 110 could represent those for the hydrogen atoms in the oil, and the nuclear magnetic moments 120 could represent those for the hydrogen atoms in the water. The rate of spin 102, in this example, would be for that of hydrogen atoms, and the Larmor frequency would be that for hydrogen.

Figure 5A:
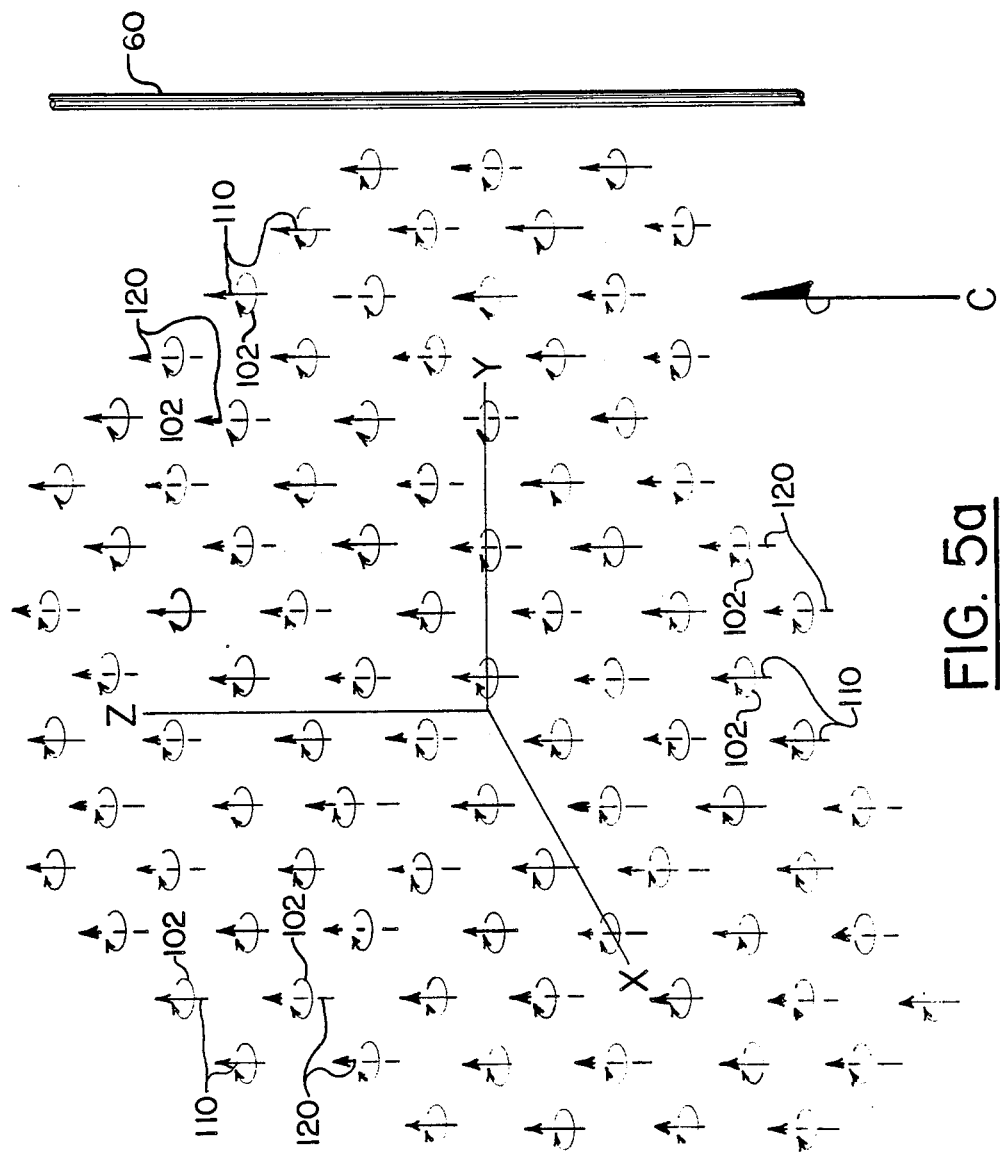

As illustrated in FIG. 5a, the mixture of the first and second materials is shown exposed to a strong constant magnetic field C. In response, the nuclei magnetic moments 110, 120 of the hydrogen atoms in the respective first and second materials become oriented in the Z direction parallel to the constant magnetic field C and start precessing at Larmor frequency about an axis parallel to the constant magnetic field C. For purposes of simplicity and clarity, these illustrations in FIGS. 5a–5g do not attempt to show the nuclear magnetic moments of other atoms present in the mixture. It also does not attempt to show nuclei magnetic moments of other hydrogen atoms in the mixture that do not orient with the constant magnetic field C. Suffice it to say that this illustration is concerned only with the hydrogen nuclei magnetic moments and that a significant statistical probability exists that a substantial number of those hydrogen nuclei magnetic moments exhibit the properties illustrated in the stages of FIGS. 5a–5g at the times and under the conditions described herein.

Figure 6:
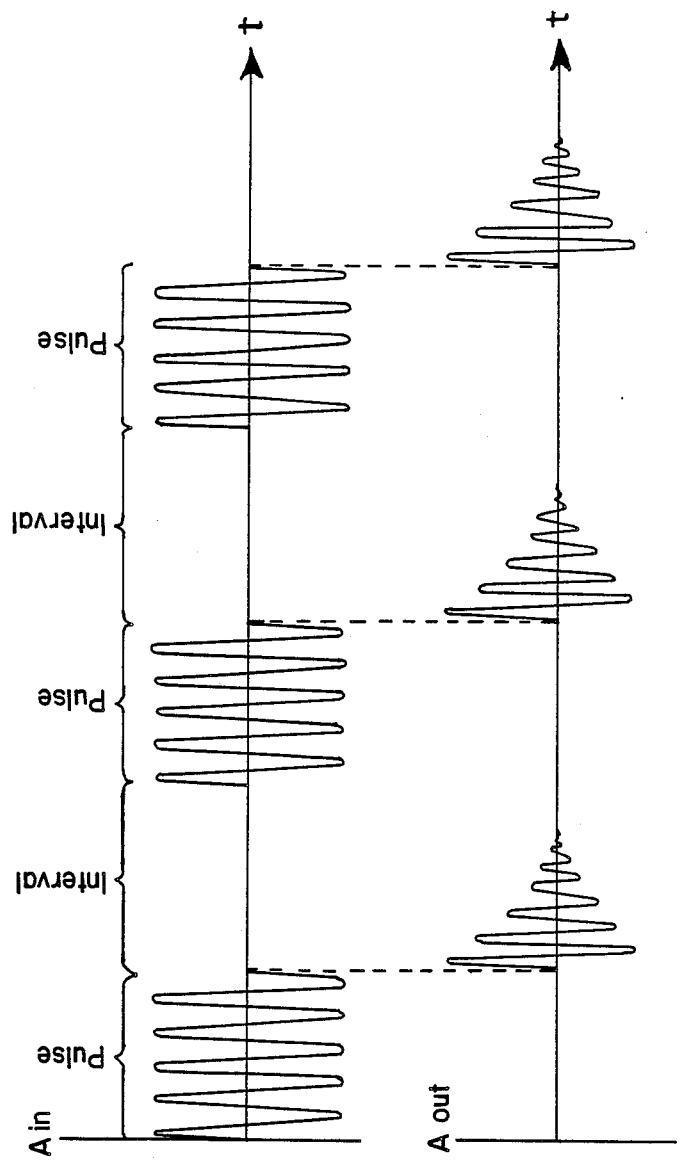
FIG. 6 shows time-amplitude representations of the rapid pulses of alternating magnetic field utilized in this invention and of the NMR emission produced by the rapid pulses of alternating magnetic field.

When a pulse of weak alternating magnetic field A oscillating at the Larmor frequency of hydrogen is first applied to the mixture perpendicular to the constant magnetic field C, as shown in FIGS. 5b and 6, the nuclei magnetic moments 110, 120 of the first and second materials, respectively, begin to tilt away from the Z-axis, which movement in combination with the initial precessing motion produces a wobbling motion similar to that of a spinning toy top. As the pulse of alternating magnetic field continues, the precessing nuclei magnetic moments 110, 120 spiral downwardly, as indicated by path 104, toward the X-Y plane perpendicular to the Z axis.

Figure 5C:
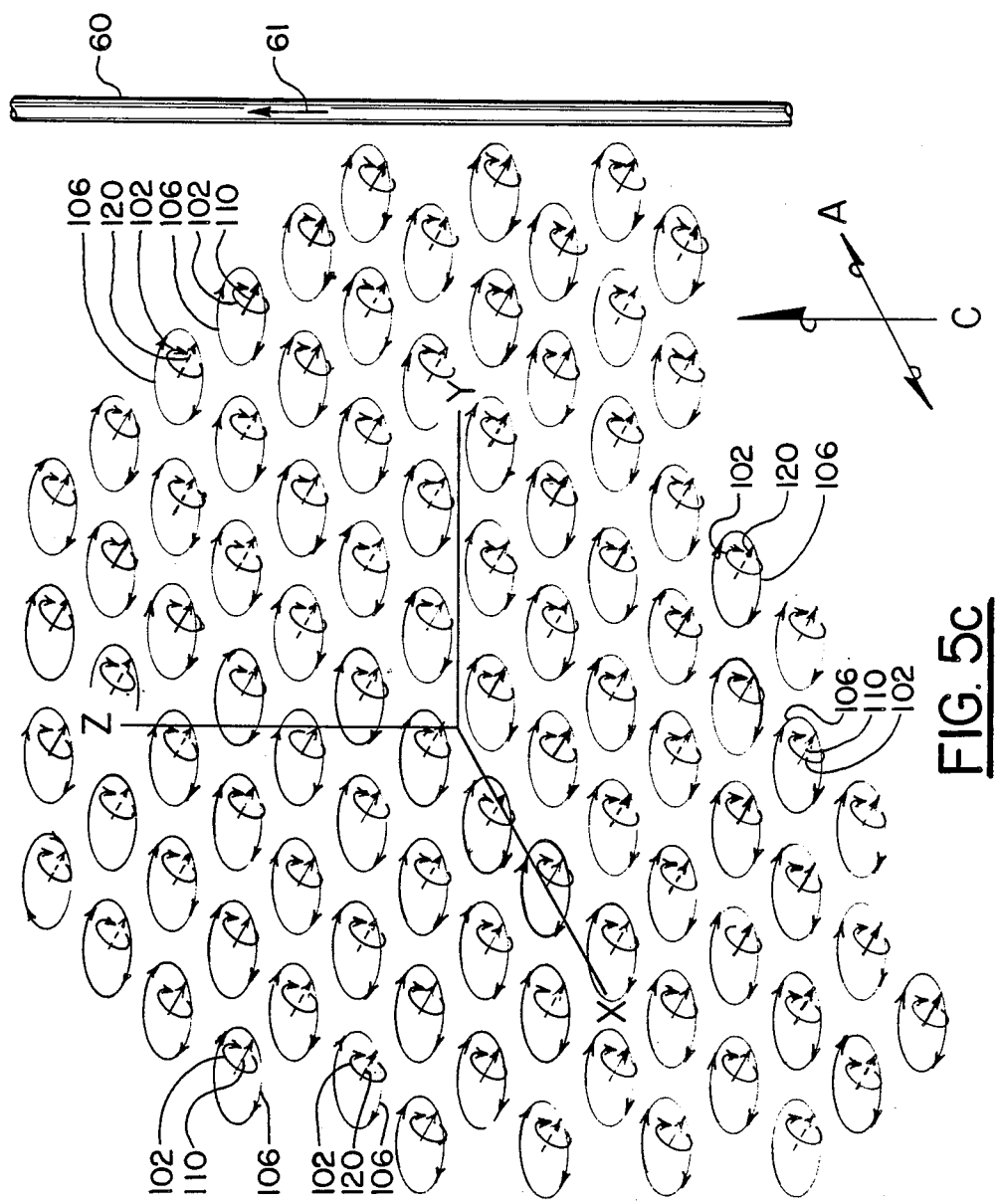

When the precessing nuclei magnetic moments 110, 120 reach the X-Y plane as a result of the first 90 degree pulse of alternating magnetic field, as illustrated in FIG. 5c, they are still oriented in substantial radial alignment with each other as they rotate or precess in circles 106 about their respective Z-axes. At this point, the pulse of alternating magnetic field can be terminated, as illustrated in FIG. 6, and the initial free induction or electromagnetic voltage or current 61 induced in the conductor 60 can be measured. It is also at this point in time that the amplitude of the induced voltage or current 61 will be greatest because it is induced by the maximum number of nuclei magnetic moments 110, 120 of both the first and second materials aligned and sweeping in unison in the X-Y plane, as illustrated in FIG. 5c. Therefore, such initial NMR emission is induced by both the first and second materials in the mixture.

Figure 5D:
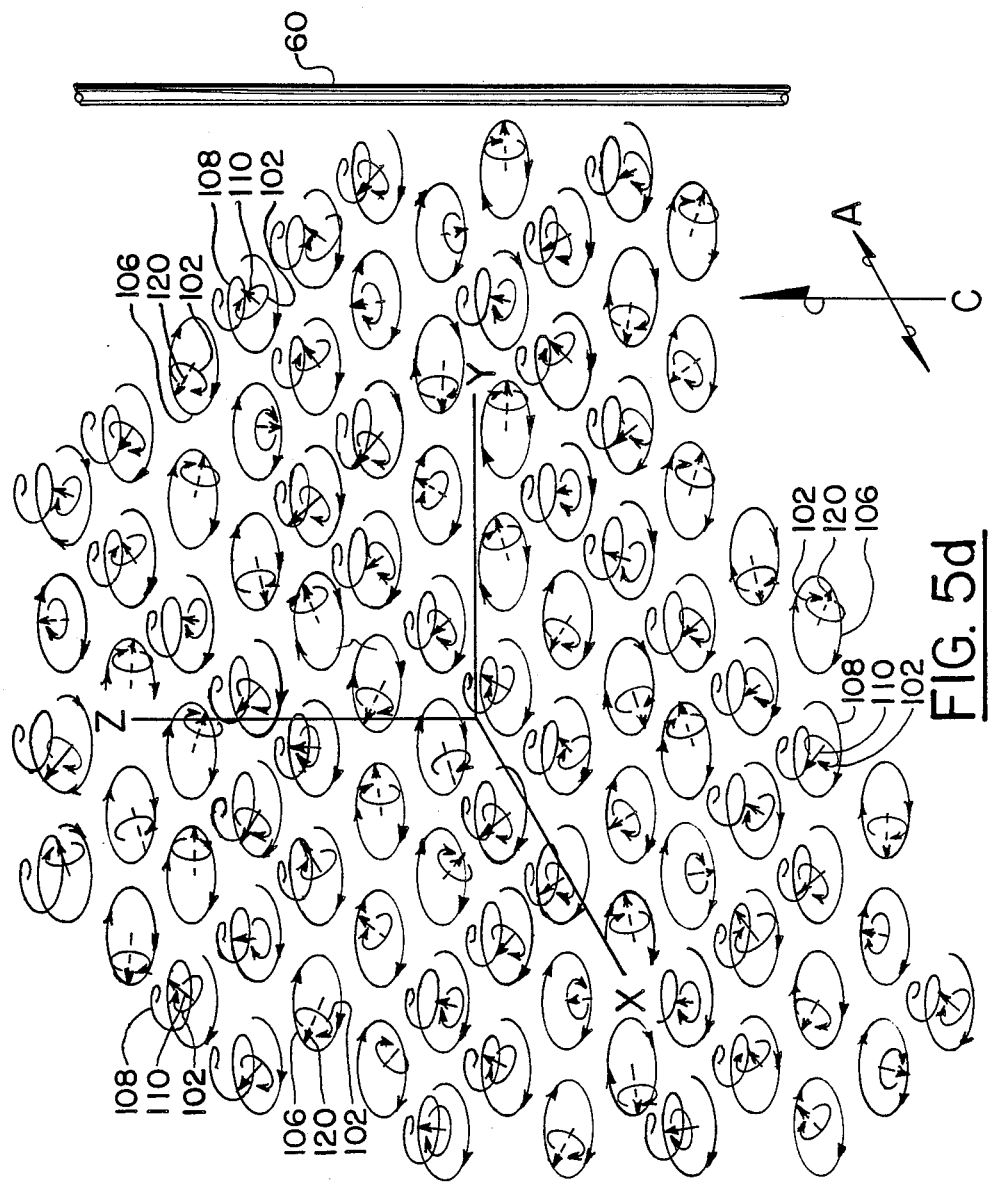

As the pause after the pulse continues, two phenomena occur simultaneously, as illustrated in FIG. 5d. The first of these phenomena is that the nuclei magnetic moments 110, 120, which initially were sweeping in unison, begin almost immediately to disalign and scramble into random orientations about their Z-axes, which randomization or dispersion is the result of small variations in the rate of precession of individual nuclear magnetic moments. An individual nuclear magnetic moment precesses at Larmor frequency that is proportional to the constant magnetic field C. Therefore, the nonuniformity in the constant magnetic field C is the major source of the aforementioned randomization. Consequently, as the nuclei magnetic moments 110, 120 randomize, there is no longer a unitary magnetic field or emission cutting the conductor 60. Instead, the randomly oriented nuclei magnetic moments 110, 120 cancel each other out, so the induced voltage or current 61 in conductor 60 diminishes.

The rapid decay of the NMR emission due to the nonuniform precession velocity is called Free Induction Decay or FID. The second of these phenomena, which occurs simultaneously with first, is that nuclei magnetic moments 110 and 120 brought down to the X-Y plane begin to relax or recover back toward the equilibrium position of the Z axis parallel to the constant magnetic field C, or they return to the random state. The progressive decay of the NMR emission due to the reorientation of the nuclei magnetic moments caused by the random or vibratory molecular movement is called Spin-Spin relaxation. The rate of Spin-Spin relaxation is faster for species with low level of random molecular motion and slower for species with high level of random molecular motion. For example, the nuclei magnetic moments 110 belonging to the first material returns to the equilibrium orientation parallel to the Z-axis following a spiral path 108 much faster than the nuclei magnetic moments 120 of the second material still holding their precessing circular paths 106 in the X-Y plane in randomly oriented radial directions, as illustrated in FIG. 5d.

Figure 5E:
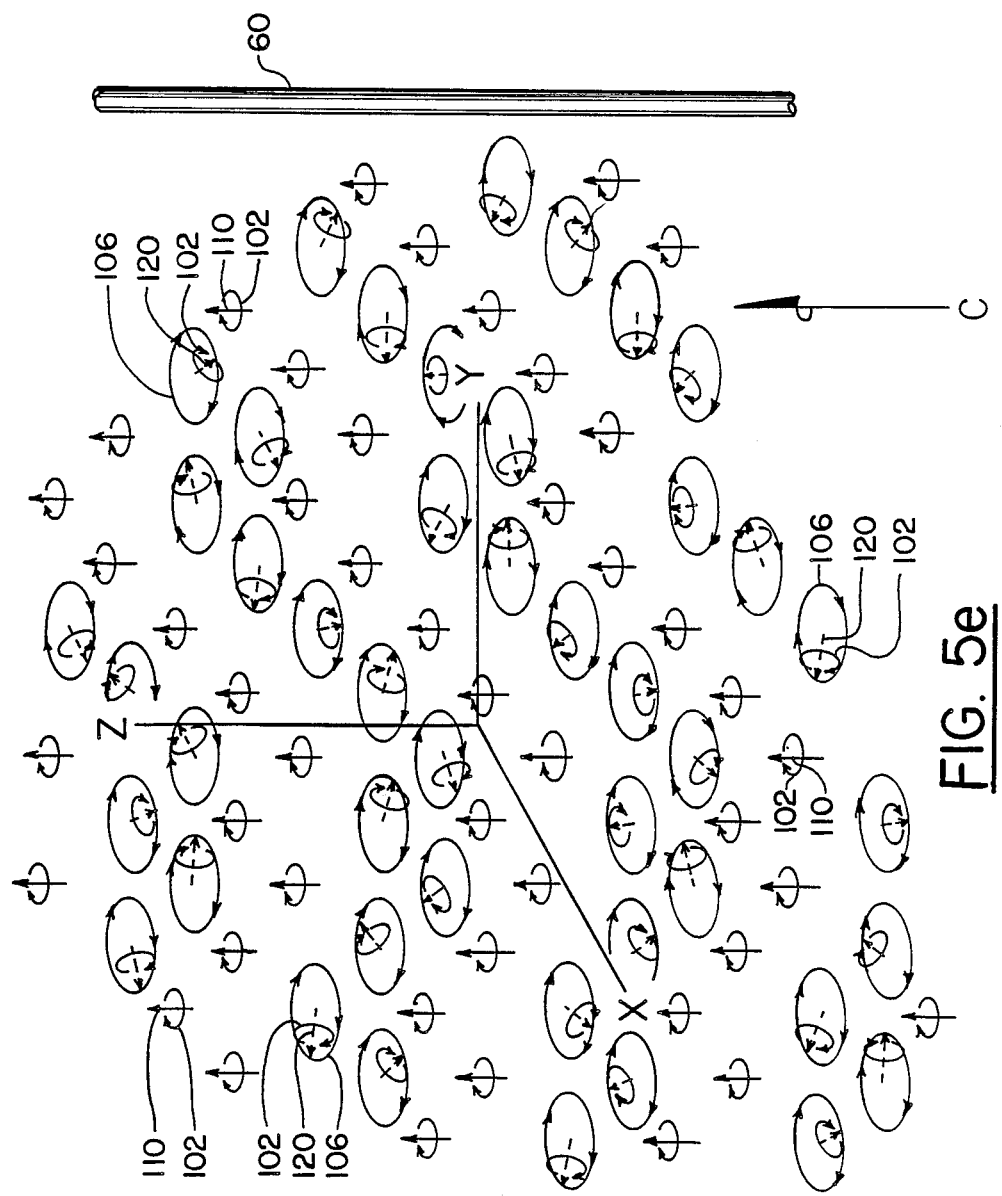

The decay of the normal component and the recovery of the parallel component of the nuclei magnetic moments following a 90 degree pulse is illustrated in FIG. 5e. The nuclei magnetic moments 110 of the common species of the first material are shown fully recovered, as indicated by the arrows 102, similar to the initial positions shown in FIG. 5a prior to the 90 degree pulse. However, the nuclei magnetic moments 120 of the common atomic species of the second material have hardly recovered as they are still precessing on the X-Y plane, as indicated by the circular path 106 in the X-Y plane. In this condition, there is no significant induced voltage or current in conductor 60, because the rotating nuclei magnetic moments 110 precessing about the Z-axis do not create rotating magnetic flux to cut the conductor 60 when they are oriented parallel to the Z-axis, and the nuclei magnetic moments 120 precessing on the X-Y plane are in random orientation as the result of FID and cancel each other out. Therefore, there is no significant measurable NMR emission in the condition of FIG. 5e, which takes place in a few hundred microseconds after the termination of the 90 degree pulse of the alternating magnetic field.

If a sufficient time interval or pause is allowed to pass with no alternating magnetic field A, the nuclei magnetic moments 120 of the second material would eventually recover also to the Z axis alignment parallel to the constant magnetic field C. The speed of the recovery of the nuclei magnetic moments to the equilibrium position or the growth of the nuclei magnetic moments in direction parallel to the constant magnetic field A is determined by the spin-lattice relaxation time. It is evident that, in order to generate an NMR emission, the 90 degree pulse of the alternating field A must be applied after allowing a significant growth or recovery of the nuclei magnetic moments to the Z-axis. If the 90 degree pulse of the alternating magnetic field A is applied to the nuclei magnetic moments under random distribution (zero recovery or growth), it will not produce an NMR emission.

A significant feature of this invention is the application of another 90 degree pulse of the alternating magnetic field A after a significant recovery of the nuclei magnetic moments 110 with fast spin-lattice relaxation and before any significant recovery of the nuclei magnetic moments 120 with slow spin-lattice relaxation. When this rapid pulse sequence occurs, only the nuclei magnetic moments of the first material will emit NMR signal.

Figure 5F:
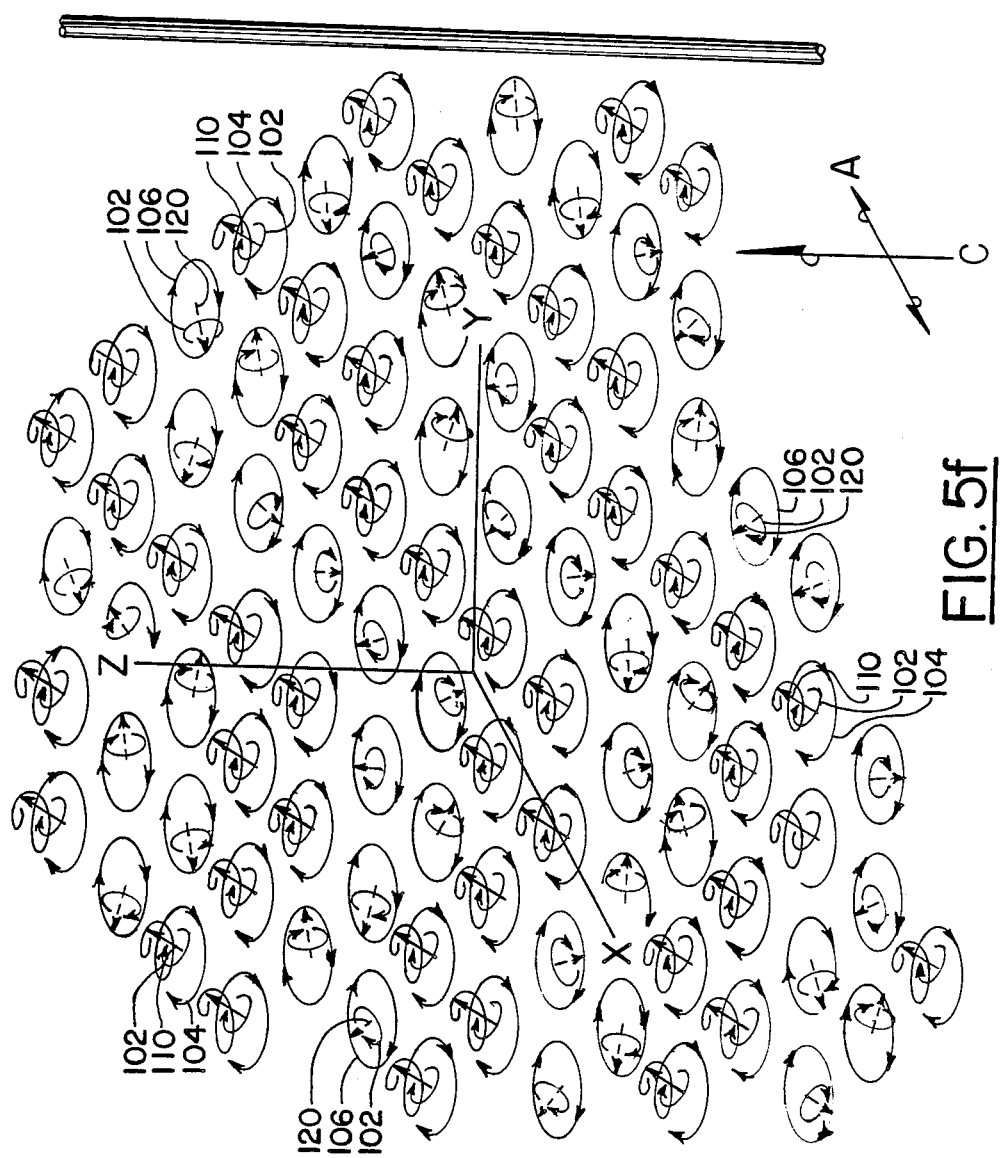

In more general explanation, it is evident that, in order to generate an NMR emission, there must exist a parallel component of the nuclei magnetic moments in an ordered assemblage at the time when a 90 degree pulse of alternating magnetic field A is applied. The 90 degree pulse of the alternating magnetic field A rotates the parallel component 90 degrees from the Z-axis to the X-Y plane. In other words, the 90 degree pulse of the alternating magnetic field changes the parallel component to the normal component. It is the normal component that produces the NMR emission. It is evident from the aforementioned facts that a series of successive pulses of the alternating magnetic field $A_{in}$, as shown in FIG. 6, with pause time between two consecutive pulses large enough for a significant recovery of the nuclei magnetic moments 110 of the first material, but small enough not to allow any significant recovery of the nuclei magnetic moments 120 of the second material, will produce NMR emission from the first material only. In FIG. 5f there is illustrated the distribution taken up by the nuclei magnetic moments under the successively pulsed alternating magnetic field immediately prior to the onset of a 90 degree pulse, wherein the nuclei magnetic moments 110 are significantly recovered back to the equilibrium orientation parallel to the Z-axis, while the nuclei magnetic moments 120 are still in a random distribution.

Figure 5G:
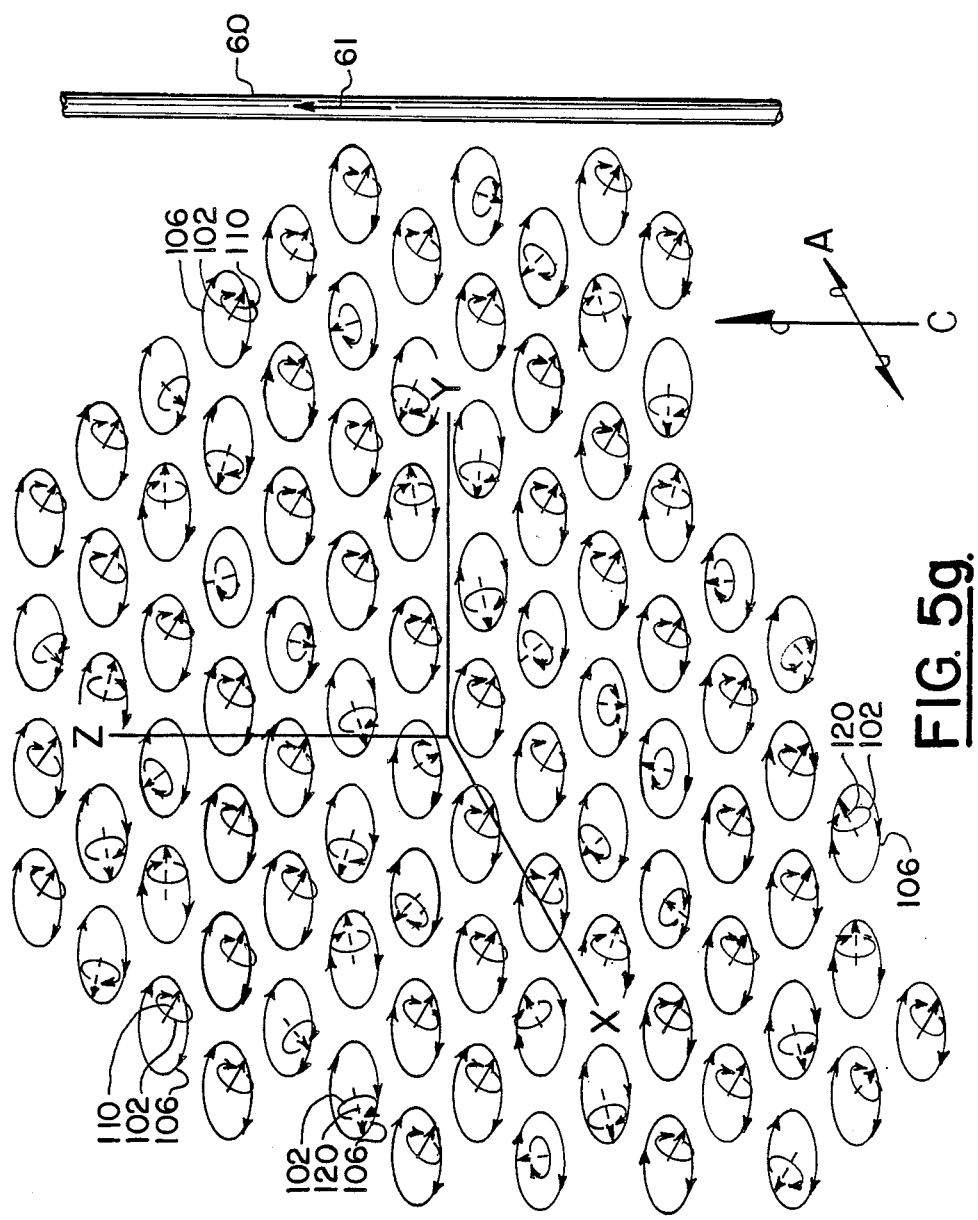

When the fully or partially recovered or grown (oriented in unison) nuclei magnetic moments 110 of the first material are brought down to the X-Y plane by a 90 degree pulse, they precess in unison, as illustrated in FIG. 5g, because they are brought down in unison. However, as also illustrated in FIG. 5g, the nuclei magnetic moments 120 of the second material are still in random relation to each other. Having never recovered to the Z axis orientation, the nuclei magnetic moments 120 distributed in random are brought down in ramdom pattern by the alternating magnetic field A. Therefore, they remain in their random orientation, and continue to cancel each other out. Meanwhile, when the 90 degree pulse is terminated, the nuclei magnetic moments 110 of the first material are aligned and rotating in unison on the X-Y plane, with combined magnetic flux cutting the conductor 60. Consequently, virtually all of the induced voltage or current 61 in conductor 60 is generated by the nuclei magnetic moments 110 of the first material. It follows, therefore, that a measure of the amplitude of the induced voltage or current 61 is a measure of the amount of the first material in the mixture.

In reviewing the process described above, there are basically two essential mechanisms associated with the nuclei magnetic moments 110, 120 of the common atomic species in the different molecular structures of the first and second materials. The first mechanism is magnetization, i.e., growth or recovery of the nuclei magnetic moments to the Z axis. The second mechanism is dispersion or randomizing of the nuclei magnetic moments after they have been tilted 90 degrees to the X-Y plane. It is essential that the nuclei magnetic moments 110 of one of the materials grow or recover back to the Z axis faster than the nuclei magnetic moments 120 of the other material. It is the strong constant magnetic field C that creates the ordered state from the random state in the orientation of nuclei magnetic moments. It is the pulse of the weak alternating magnetic field A that generates NMR emission from the nuclei magnetic moments 110 in an ordered state and maintains the random state of the nuclei magnetic moments 120.

A requirement of this invention, therefore, is to apply rapidly repetitive successive pulses of alternating magnetic field of amplitude $A_{in}$ at the Larmor frequency of the common atomic species to the mixture as shown in FIG. 6. The pulses are preferably 90 degree pulses, i.e., sufficient to energize the nuclei magnetic moments of the common atomic species to tilt 90 degrees to the X-Y plane. However, there should be only enough time or pause between pulses to allow substantial recovery only for the nuclei magnetic moments 110 of the first material to the Z-axis, but not enough time for the nuclei magnetic moments 120 of the second material to make any significant amount of recovery toward the Z-axis. Therefore, the NMR emissions from the material generated by the rapidly repetitive successive pulses will be essentially entirely from the first material which NMR emission $A_{out}$ decays rapidly due to FID phenomenon, as shown in FIG. 6. The initial peak amplitude of the NMR emission $A_{out}$ is directly proportional to the total number of the nuclei magnetic moments 110 and, consequently, to the abundance of the first material in the mixture.

With this set-up, the NMR emission in the form of the free induction decay (FID) of the first material in the mixture is detected by amplifying at 66 detecting at 67, and amplifying again at 68, and measured and processed at 69 in a continuous and real time mode, as illustrated in FIG. 3. The amplitude of the emission in NMR analysis is, of course, indicative of the amount of the material present from which the emission is generated. The more emitting material present, the higher will be the NMR emission amplitude. To relate this phenomenon to the above description, the more nuclei magnetic moments 110 there are in the mixture, the stronger will be the magnetic flux field cutting the conductor 60, thus emitting a stronger signal that is directly proportional to the abundance of the first material in the mixture.

The fraction or cut of the emitting material in a total mixture, therefore, can be determined by comparing the maximum amplitude of the NMR emission from a volume of the mixture with the maximum amplitude of NMR emission from an equal volume of 100% of the material exposed to the same NMR conditions. Therefore, only the maximum amplitude of the NMR emission at the beginning of the free induction decay (FID) is required, i.e., the FID peak measurement, for determining the fraction or cut of the emitting material. Measurement of the entire FID envelope and extrapolation back in time to the beginning of the decay to separate the portions of the FID peak contributed by each material in the mixture is not necessary.

The apparatus shown in FIGS. 1 and 2 are designed for using this rapid pulse NMR analysis technique on a flowing fluid mixture to obtain a real-time continuous measurement of the fraction or cut of one of the materials in the mixture. The mixture is flowed through the tube container 20 into an area of a strong, constant magnetic field oriented transverse to the tube 20 and induced by the permanent magnet bank 40. Upon entering this zone, a statistically large probability of the nuclei magnetic moments in the mixture orient to the equilibrium orientation parallel with the constant magnetic field and, consequently, attain an intermediate energy level higher than the state with no constant magnetic field.

Then, as the fluid continues to flow through the tube 20, it enters the zone of an alternating magnetic field produced by the rf transmission coil 50. The alternating magnetic field is directed parallel to the longitudinal axis of the tube 20 and perpendicular to the transverse constant magnetic field. The rf generator 56 is set to oscillate at the Larmor frequency of the common atomic species. The pulse generator 58 is set to intermittently close the switch 59 long enough for a 90 degree pulse, i.e., to impart enough energy to tilt the nuclei magnetic moments of the common atomic species through 90 degrees from the direction of the constant magnetic field to the plane perpendicular to the constant magnetic field and, thus, elevating the energy level to a high level. The pulse generator 58 then opens the switch 59 for a pause or time interval long enough to allow the reduction of energy level from the high level to the intermediate level, in which pause time the nuclei magnetic moments 110 of the common atomic species in first material significantly realign back to the parallel alignment with the constant magnetic field, but not long enough to allow any such significant recovery or realignment of the nuclei magnetic moments 120 of the common atomic species in the second material. The energy released during the transition from the high energy level to the intermediate energy level (the recovery process back to the equilibrium orientation) is emitted in the form of a radio frequency electromagnetic wave of Larmor frequency, that is NMR emission. The initial dwell time or exposure of any cross section of the mixture flowing in the tube to the alternating magnetic field should be long enough to create a completely random state for the nuclei magnetic moments 120 of the common atomic species in the second material. Such dwell time is preferred to be at least two pulses.

In this state, with the nuclei magnetic moments 120 of the second material scrambled to random orientations and the nuclei magnetic moments 110 being alternately tilted to the perpendicular plane and allowed to realign to the constant magnetic field by the intermittent times pulses of alternating magnetic field, the mixture flows into the zone of the receiver coil 60. In this zone, within the alternating magnetic field produced by the transmission coil 50, the NMR emissions from the mixture are detected by the receiver coil 60. These detected signals are amplified by an rf amplifier 66 and fed into a detector 67. The detector 67 detects the envelope of the rf and feeds the envelope signal to an audio amplifier 68 and then to a data processor 69. Since the nuclei magnetic moments 120 of the common atomic species in the second material are maintained in a dispersed, randomized state without allowing any significant amount of growth, the detected NMR emission is from the nuclei magnetic moments 110 of the common atomic species in the first material.

The data processor 69 can be used to perform a number of useful functions. For example, it can store the maximum amplitude of NMR emissions or FID peak from a sample of 100% of the first material flowing through the probe 10 under the same conditions and compare the stored information with the actual NMR emission from the mixture in determining the fraction or cut of the first material in the mixture. For mixtures where quality of materials changes over time, a system can be set up to gather such reference data representing the 100% samples of the first material and feed those data to the processor for periodically updating the maximum amplitude or FID peak value stored and used in the data processor 69 for cut point determinations. Of course, the cut point meter of this invention can also be paired with a volumetric flow meter (not shown), so that the data processor could use the cut point determinations to determine flow rates and flow volumes of the first material in the mixture on a real-time continuum.

The example of using this rapid pulse nuclear magnetic cut meter technique for measuring fraction or cut point of an organic material, such as oil, in a mixture with an aqueous material, such as water, was mentioned above. In such an application, this invention solves the long-standing problem of measuring oil cut point on a real-time basis in a two-or three-phase flow in an oil well production flow line or gathering system in which crude oil, along with substantial quantities of salt water and some mud, sand, and other materials are typically produced by an oil well.

The hydrogen atoms with $+\frac{1}{2}$ spin (parity) in oil, water, and natural gas emit NMR rf waves. In general, the number of hydrogen atoms in gaseous phase is insufficient, and the level of the random motion is too high, to generate any NMR emission of detectable intensity. However, the oil and water in the mixture generate NMR rf emissions of intensity comparable to each other at the same Larmor frequency. The spin-lattice relaxation time of the hydrogen nuclei magnetic moments in oil is less than 50 milliseconds, while that for water is several seconds, which implies that oil recovers back to the initial state of intermediate energy level induced by the constant magnetic field much faster than water after a mixture of these two materials has been boosted to a higher energy level by rf transmission, i.e., alternating magnetic field. Therefore, if the rf transmission is composed of a series of intermittent 90 degree pulses with such a short pause time between each pulse that water, with its long recovery time, hardly recovers at all, while oil experiences substantial recovery back to or toward the initial state of intermediate energy level or equilibrium, then only the oil will emit rf or NMR emission. In other words, because water, due to the rapid repeating 90 degree pulses of rf transmission, hardly experiences any recovery at all, it only absorbs very little energy from each successive rf transmission. Consequently, water emits very little NMR emission.

Indeed, water is virtually transparent to a series of 90 degree pulses of rf transmissions when the pause time or interval between successive 90 degree pulses is less than 20 milliseconds. In fact, it has been found that such a train of rapid 90 degree pulses of rf transmissions with 20 milliseconds pause time between pulses generates rf emission from water with amplitude of about one percent of that from oil of the same volume at room temperature. Further, the rf emission from water generated by rapid pulse rf transmission with 10 millisecond pause times is less than 0.5 percent of that from oil of the same volume at room temperature. Further, at elevated temperatures higher than 140° F., the rapid pulse rf transmissions with pause time in this 10 to 20 millisecond range does not produce any rf emission of detectable level from water.

Therefore, the rapid pulse NMR cut meter according to this invention, when set to generate rf transmission at the Larmor frequency of hydrogen in intermittent 90 degree pulses with no more than 50 millisecond (preferably 10 to 20 millisecond) pauses between pulses, does function as a genuine oil cut meter. Under these conditions, it generates NMR rf emission from oil only without generating any significant amount of NMR rf emission from water. Such rapid pulse rf transmission also does not energize other components of an oil well production, such as mud, sand, and the like. Therefore, it is a meter that actually detects and measures only oil in the mixture. This device, while operating on very powerful principals, is relatively simple in construction and requires little maintenance, tune-up, or racalibration.

The oil-cut or fraction of the mixture is determined simply by the ratio of the initial maximum amplitude, i.e., FID peak, of the rf emission from the mixture flowing through the NMR probe 10 to the FID peak of the rf emission from a sample of 100% oil flowing through the same NMR probe conditions. The FID peak of the 100% oil sample can be stored in the computer or data processor 69. If the quality or characteristics of the oil produced from a particular well vary over time, this FID peak value representing 100% oil can be updated periodically as desired by flowing a new sample of 100% oil through the probe 10 and storing such data in the processor memory.

The amplitude of the NMR emission from oil other than the initial peak thereof may also be employed in analyzing the oil cut. For example, a combination of 90 degree and 180 degree pulses may be transmitted in a series of rapid pulses instead of 90 degree pulse, and the spin echo peak instead of FID peak may be detected and analyzed to determine the oil cut.

The foregoing is considered as illustrative only of the principles of the invention. Further, since numerous modifications and changes will readily occur by those skilled in the art, it is not desired to limit the invention to the exact construction and operation shown and described, and accordingly, all suitable modifications and equivalents may be resorted to falling within the scope of the invention as defined by the claims which follow.

The embodiments of the invention in which an exclusive property or privilege is claimed are defined as follows:

1. A method for determining the amount of organic material in a mixture that includes organic and aqueous material, comprising the steps of:

exposing the mixture continuously to a strong constant magnetic field to cause the nuclei magnetic moments of hydrogen atoms in the mixture to be oriented about parallel to the constant magnetic field;

while said mixture is exposed to said constant magnetic field, simultaneously exposing said mixture to rapidly repeated pulses of an alternating magnetic field that alternates at about the Larmor frequency of the hydrogen atoms with pulse durations sufficient to reorient the nuclei magnetic moments of the hydrogen atoms in the mixture approximately 90° away from the positions parallel to the constant magnetic field and with the time intervals between successive pulses being sufficiently long to allow substantial recovery of the nuclei magnetic moments of hydrogen atoms in the organic molecules so that the material emits substantial measurable rf emission associated with said organic molecules, and with said time intervals being too short to allow any significant recovery of the nuclei magnetic moments of the hydrogen atoms in the aqueous materials and other nonorganic materials so that there is no significant rf emission from the mixture associated with the hydrogen atoms in the aqueous and nonorganic materials;

detecting and measuring the rf emissions from said mixture; and determining the fraction of the mixture comprising the organic material by comparing the maximum amplitude of the detected rf emissions from the mixture after said pulses subsequent to the first pulse with a known standard value of maximum amplitude emission from a sample constituting 100 percent of the organic materials in the mixture exposed to the same conditions as the mixture.

2. A method for determining the amount of a first material in a flowing stream of a mixture that includes said first material and a second material, wherein said first and second materials have different molecular structure with an atomic species that is common to each molecular structure, wherein the nuclei magnetic moments of said common atomic species have the same Larmor frequency, but the nuclei magnetic moments in said first material have a faster NMR spin-lattice relaxation time than the nuclei magnetic moments of the common atomic species in said second material, comprising the steps of:

flowing the mixture in a conduit through a length of strong, constant magnetic field that is oriented in a first direction long enough to orient the nuclei magnetic moments of said common atomic species toward an equilibrium;

while said mixture is flowing through said conduit in said constant magnetic field, simultaneously exposing said mixture to rapdily repeated, intermittent pulses of an alternating magnetic field that is oriented in a second direction and which oscillates at about the Larmor frequency of the common atomic species;

making said successive intermittent pulses of durations sufficient to energize and reorient the nuclei magnetic moments out of the equilibrium imposed by the constant magnetic field and with time intervals between the successive pulses long enough to allow substantial recovery of the nuclei magnetic moments of the common atomic species in the first material back toward said equilibrium, but not long enough for any significant recovery of the nuclei magnetic moments of the common atomic species in the second material;

after a cross section of said mixture has flowed through said strong, constant magnetic field long enough to orient said nuclei magnetic moments of said common species toward said equilibrium and after said cross section has been exposed to at least two of said pulses, flowing said cross section of fluid into the vicinity of a receiving antenna; and detecting and measuring the NMR emissions received by said antenna from said mixture between said pulses.

3. The method of claim 2, including the step of applying at least 20 pulses per second.

4. The method of claim 2, wherein said time interval between pulses is less than 50 milliseconds.

5. The method of claim 4, wherein said time intervals between pulses are in the range of about 5 to 20 milliseconds.

6. The method of claim 2, including the step of flowing said mixture through said constant magnetic field with the relationship between the flow rate and the length of the constant magnetic field being sufficient to expose any cross section of said flowing mixture to said constant magnetic field for at least 5 milliseconds before exposing the mixture to said alternating magnetic field.

7. The method of claim 2, including the step of measuring the initial maximum amplitude of the NMR emission of the mixture detected and measured between pulses and comparing said initial maximum amplitude from the mixture with the initial maximum amplitude of a sample of a like volume of 100 percent of the first material exposed to the same conditions to determine the fraction of the first material in the mixture.

8. The method of claim 7, including the step of applying said pulses as 90 degree pulses.

9. The method of claim 8, including the steps of continuously flowing said mixture through said constant and alternating magnetic fields and continuously detecting and measuring said NMR emissions from the mixture and comparing them to emissions from a 100 percent sample to obtain continuous measurements of first material fraction in the mixture on a real-time basis.

10. The method of claim 9, including the steps of simultaneously measuring volumetric flow rate of the mixture and multiplying the volumetric flow rate of the mixture by the fraction of first material to obtain volumetric flow rate of the first material in the mixture.

11. The method of claim 9, including the steps of simultaneously measuring volumetric flow of the mixture and multiplying the volumetric flow by the fraction of first material to obtain volumetric flow of the first material in the mixture.

12. The method of claim 2, including the step of exposing the mixture to the constant magnetic field of about 10 to 10,000 gauss and to the alternating magnetic field of about 1/1000th the strength of the constant magnetic field.

13. Apparatus for determining on a real-time basis the fraction of a first material in a flowing mixture that includes said first material and a second material, wherein said first and second materials have different molecular species with a common atomic species, the common atomic species in the molecular species having the same Larmor frequency, but different NMR spin-lattice relaxation times; comprising:

elongated, flow-through conduit means for containing and confining the flowing mixture;

constant magnetic means adjacent a substantial length of said conduit means for producing a strong, constant magnetic field oriented in a first direction along said substantial length and through said mixture flowing in said conduit means;

alternating magnetic means adjacent both said conduit means and said constant magnetic means for producing a weak alternating magnetic field applied in intermittent pulses of timed duration in a second direction along a substantial length of said conduit means and through said mixture flowing in said conduit means;

frequency control means connected to said alternating magnetic means for controlling the frequency of said alternating magnetic field substantially equal to the Larmor frequency of said common atomic species in said mixture;

pulse control means connected to said alternating magnetic means for controlling the duration of each of said pulses to about the time required to tilt the nuclei magnetization of said common atomic species from said first direction to a plane including said second direction, and for controlling the time intervals between successive pulses to a time period which is long enough for one of said molecular species to generate NMR output emission of substantial measurable level, but which is not long enough for the other of said molecular species to generate any significant measurable NMR output emission;

receiver means positioned adjacent said conduit means in the vicinity of said alternating magnetic means for detecting said NMR output from said one of said molecular species, said receiver means being much shorter than said constant and said alternating magnet means and positioned adjacent said conduit at a location where said constant and alternating magnetic fields extend substantial lengths upstream and downstream from said receiver means.

14. The apparatus of claim 13, including processor means connected to said receiver means for converting maximum amplitudes of said NMR output to data that indicates the amount of said one of said molecular species in the mixture by comparing said maximum amplitudes to the maximum amplitude of NMR output of a known 100% of the molecular species exposed to, and measured in, the same conditions.

15. The apparatus of claim 13, wherein said conduit means includes an elongated tube that is open at both ends and adapted for connection to a flow pipe that carries a flowing stream of the mixture.

16. The apparatus of claim 15, wherein said constant magnetic means includes a strong magnet positioned adjacent a substantial length of said elongated tube, said alternating magnetic means is comprised of a transmission coil of electrical conductor material wound around the periphery of the tube, and said receiver means is comprised of a receiver coil of electrical conductor material wound around the periphery of a very short length of the midportion of the tube, there being a sufficient length of said magnet and said transmission coil extending in both upstream and downstream directions from said receiver coil that any cross-section of the mixture flowing through the tube is exposed to, and maintained in, said strong, constant magnetic field and concurrently to at least two pulses of said alternating magnetic field before reaching a range where NMR emission from such cross-section of mixture interacts with said receiver coil and to keep said cross section exposed to the magnetic fields of said magnet and said transmission coil until it has passed out of the range of said receiver coil.

17. The apparatus of claim 16, wherein said magnet extends along substantially the entire length of said tube, said transmission coil is comprised of a first segment and a second segment, said first segment extending from a spaced distance inwardly from one end of the magnet to near the midportion of the tube, and said second segment extending from a spaced distance inwardly from the other end of the magnet to near the midportion of the tube, leaving a short gap between said first and second segments at the midportion of the tube, and said receiver coil being positioned in said short gap at the midportion of the tube.

* * * * *